United States Patent [19]

Mohler

[11] 4,235,114

[45] Nov. 25, 1980

[54] MATERIAL TESTING DEVICE

[75] Inventor: David B. Mohler, Tipp City, Ohio

[73] Assignee: Ledex, Inc., Vandalia, Ohio

[21] Appl. No.: 26,254

[22] Filed: Apr. 2, 1979

[51] Int. Cl.³ .............................................. G01N 3/08
[52] U.S. Cl. ......................................... 73/805; 73/826
[58] Field of Search ................. 73/826, 770, 771, 827, 73/831, 832, 806, 805

[56] References Cited

U.S. PATENT DOCUMENTS

| | | |
|---|---|---|
| 3,416,052 | 12/1968 | Russell et al. . |
| 3,541,841 | 11/1970 | Taoka et al. ........................ 310/24 X |
| 3,630,074 | 12/1971 | Hartman ................................ 73/805 |
| 3,864,608 | 2/1975 | Normile et al. . |
| 3,870,931 | 3/1975 | Myers . |
| 4,048,848 | 9/1977 | Dybel .................................... 73/770 |

Primary Examiner—Jerry W. Myracle
Attorney, Agent, or Firm—Biebel, French & Nauman

[57] ABSTRACT

A testing device for applying a force to a material test sample includes a test fixture for engaging the test sample and a solenoid, operatively coupled to the test fixture, for applying a predetermined force to the test sample in response to a solenoid control signal. A strain gauge is mounted on the test fixture and provides an electrical output indicative of the force applied to the test sample. A force setting circuit provides an electrical output indicative of the predetermined force which is to be applied to the test sample. A solenoid control circuit is responsive to the output from the strain gauge element and to the output of the force setting element and provides a control signal to the solenoid such that the predetermined force may be applied to the test sample. The force setting circuit provides an electrical output having an adjustable rate of increase and an adjustable maximum level. A sample circuit monitors the output of the strain gauge to store the peak force applied to the test sample. The testing device also includes a circuit for providing a visual indication of whether the test sample has withstood an adjustable force level.

8 Claims, 4 Drawing Figures

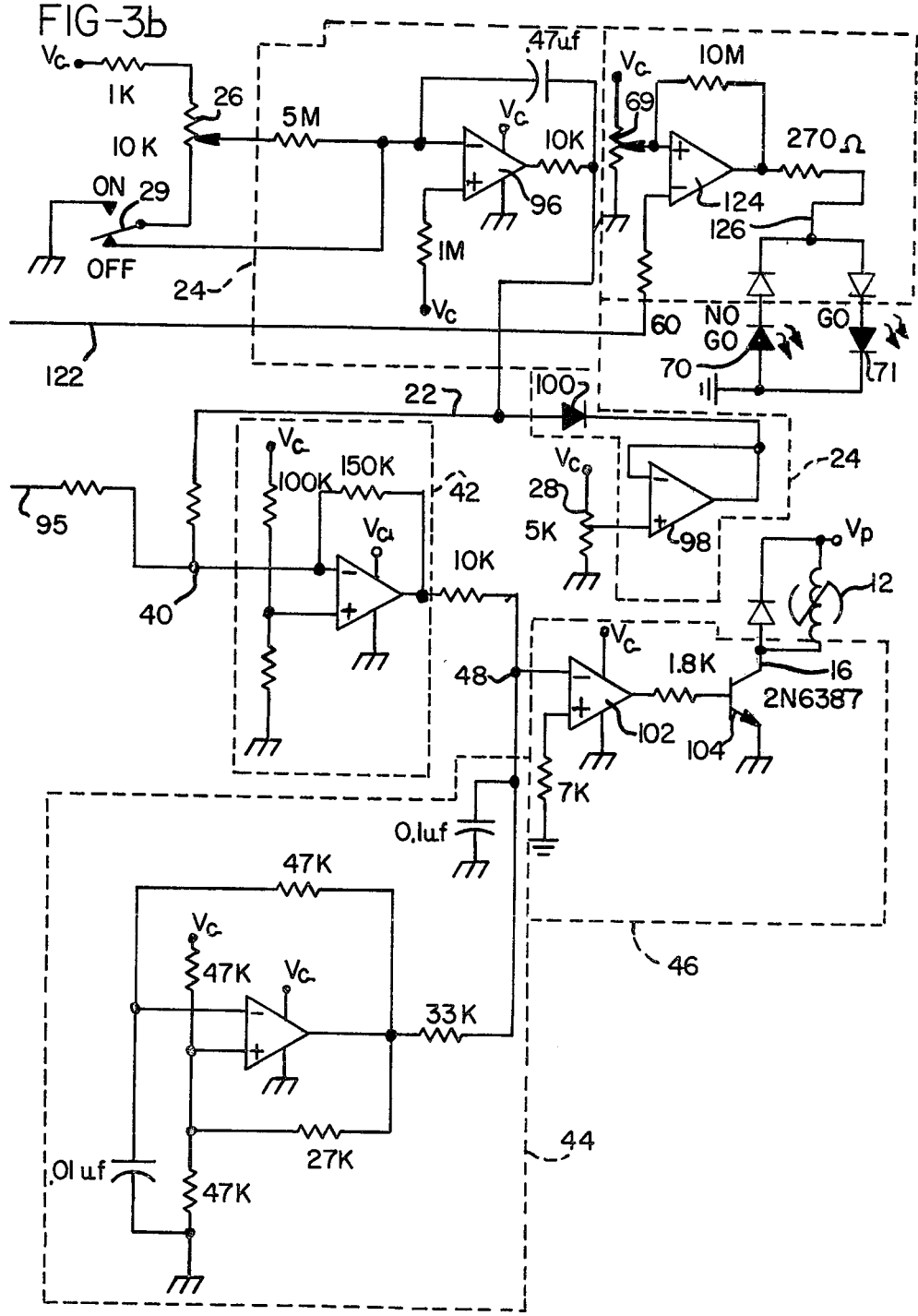

MATERIAL TESTING DEVICE

BACKGROUND OF THE INVENTION

The present invention relates to material testing devices and, more particularly, to a test device utilizing a solenoid for applying a test force to a material sample in a predetermined manner and for monitoring the effect of such force upon the sample.

Testing of many materials and machine components includes tests to determine the ability of the test samples to withstand either tensile or compressive forces, or both. Prior art devices capable of performing such tests have generally been complex in design and correspondingly expensive. One type of prior art testing device uses a test fixture including a pair of material-gripping jaws. One of the jaws is held stationary while the other jaw is moved by means of a servomotor rotating a threaded bolt which passes through the jaw mounting structure. A load cell is provided on the test fixture for monitoring the amount of force applied to the test material and providing an electrical output proportional thereto. Although this type of testing device permits a substantial range of force to be applied to the test material, control of the servomotor mechanism requires complicated control circuitry if the force applied to the test material and the rate of application of the force are to be controlled precisely.

Other testing devices utilizing hydraulic actuators for applying force to the test samples have also been used in the past. In one prior art system, a servovalve controls application of hydraulic fluid to the hydraulic actuator under control of a closed loop control circuit receiving an input from a load cell mounted on the test fixture. It will be appreciated that such a hydraulic system, while providing for substantial application of force to a test sample is large in size and presents significant problems with respect to the accuracy of force applied by the hydraulic actuator. The advantage of such a system over the servomotor type of testing device is that the hydraulic actuator may be connected directly to one of the material-gripping jaw mechanisms, thus eliminating the need for the threaded rod configuration required in the servomotor system and the attendant limitations on force level fluctuation resulting from inertia of the rod and servomotor.

Although the large prior art systems described above provide for material testing over large ranges of force levels, a need exists for a small, simple, and relatively inexpensive test device for applying a small test force to a material sample in which the material sample will experience minimal dimensional distortion. Such a device should be capable of providing extremely accurate force levels and force application rates and, further, should provide for storage of the maximum force level obtained, in the event of sample failure. It is also desirable to provide a pass/fail indication as well as a direct read out of the force level applied in order to minimize operator fatigue where a large number of samples are to be tested.

SUMMARY OF THE INVENTION

A testing device for applying a force to a material test sample which is to be tested includes a test fixture for engaging the test sample and a solenoid, operatively coupled to the test fixture, for applying a force to the test sample in response to a solenoid control signal. A strain gauge means, mounted on the test fixture, provides an electrical output indicative of the force which is to be applied to the test sample. A solenoid control circuit means, responsive to the output from the strain gauge means and to the output from the force level setting means, provides a solenoid control signal to the solenoid, thus insuring that a predetermined force is applied to the test sample.

The solenoid control circuit means may comprise means for providing a pulse width modulated solenoid control signal to the solenoid. A force setting circuit means includes means for providing an increasing electrical output and means for setting the rate of increase of the increasing electrical output, as well as means for limiting the increasing electrical output to an adjustable maximum level. The rate at which force is applied to the test sample and the maximum force level are thereby controlled.

A display means, responsive to the strain gauge means, provides a visual display of the force applied to the material. A sample means, responsive to the strain gauge means, monitors the output from the strain gauge means and provides a peak signal indicative of the maximum output of the strain gauge means. A switch means selectively connects the sample means to the display means, whereby the peak force applied to or sustained by the material may be displayed after the testing of the material is completed.

An adjustable pass level setting means provides a pass level signal indicative of a force level which the material must withstand to pass successfully. A second switch means, responsive to the strain gauge means and to the sample means, selectively provides the peak signal or the output of the strain gauge means to the output of the second switch means. A comparator means is responsive to the pass level signal and to the output of the second switch means for providing a pass indication signal when the output of the second switch means exceeds the pass level signal. A pass indicator means, responsive to the pass indication signal, provides a visual indication of whether the force applied to the material exceeds the force level set by the adjustable pass level setting means.

It is an object of the present invention to provide a testing device for applying a force to a material test sample by means of a solenoid device; to provide such a testing device in which the rate of application of force to the material test sample is controlled; to provide such a testing device in which the maximum force applied to the material test sample is controlled; to provide such a testing device in which the peak force applied to the material test sample is monitored and stored; to provide such a testing device in which a visual indication of either the peak force or the instantaneous force applied to the sample material may be displayed; to provide such a testing device in which a pass/fail visual display is provided; and, to provide such a testing device in which a closed loop control system supplies a pulse width modulated energization signal to the solenoid.

BRIEF DESCRIPTION OF THE DRAWINGS

FIGS. 3A and 3B, when assembled with FIG. 3A to the left of FIG. 3B, illustrate the circuitry of the testing device of the present invention in greater detail.

DETAILED DESCRIPTION OF THE PREFERRED EMBODIMENT

Figure 1:
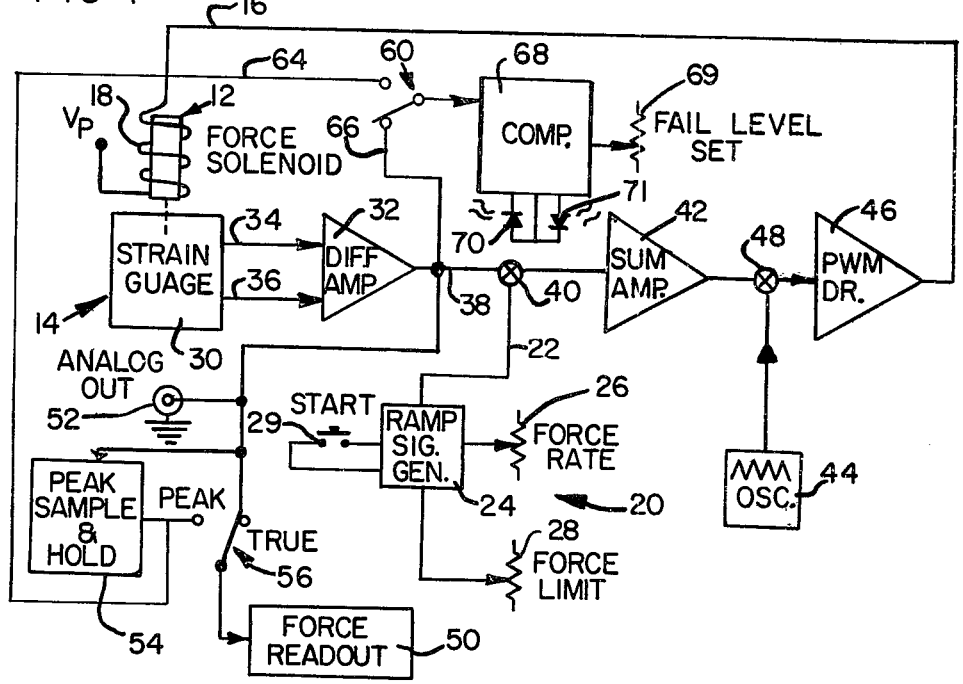
FIG. 1 is a block diagram illustrating the major components of the testing device of the present invention.

FIG. 1 illustrates the major components of the testing device of the present invention in block diagram form. A test fixture (not shown) engages the material test sample which is to be tested between a solenoid 12 and a strain gauge means 14. When the solenoid control signal on line 16 drops to ground potential, a current will flow through the coil 18 of the solenoid 12 from solenoid power source $V_p$ and a force is applied to the test sample.

A force setting circuit means 20 provides an electrical output on line 22 indicative of the force which is to be applied to the test sample. The force setting circuit means 20 includes a ramp signal generator 24 and controlling resistors 26 and 28. When start switch 29 is actuated, the ramp signal generator 24 will apply a ramp function output on line 22, the rate of increase of which is determined by the setting of resistor 26. The output signal on line 22 will increase until an adjustable maximum level is reached, as set by resistor 28.

Strain guage means 14 includes a strain gauge 30 and a differential amplifier 32, responsive to a pair of electrical output signals on lines 34 and 36. Differential amplifier 32 provides a DC signal on line 38 which is related to the force applied by the solenoid 12 to the test sample. Signals on lines 38 and 22 are added at node 40 and applied to a solenoid control circuit means which includes summing amplifier 42, saw tooth oscillator 44, and pulse width modulator driver 46. Driver 46 provides a pulse width modulated solenoid control signal to line 16 for controlling the force applied to the test sample by the solenoid 12.

The combined outputs from the strain gauge means 14 and the force setting circuit means 20 control the DC level output from summing amplifier 42 such that this DC level is impressed upon the oscillator 44 output at node 48. The pulse width modulator driver 46 will provide a grounded output control signal on line 16 to solenoid 12 whenever the input to the driver 46 exceeds a preset level. It is clear, therefore, that the force setting circuit means 20 in conjunction with the strain gauge means 14 and the solenoid control circuit make up a feedback control loop which insures that the force applied to the test sample is equal to that which is set by the force setting circuit means 20.

A force read out display means 50 provides a visual display of the force applied to the test sample. The display means 50 may comprise a conventional ammeter calibrated to display the force applied to the test sample in pounds, grams, or other units. Alternatively, a digital display may be utilized. Connector 52 is also provided for connecting the output of the strain gauge means 14 to a strip chart recorder, or other recording device.

It may often be desired to test destructively various materials by applying a force to the test sample which will cause the sample to fail. In such a testing procedure, it is desirable to store the maximum force applied to the test sample prior to failure of the sample so that this peak force level can be accurately determined. Accordingly, a peak sample and hold circuit 54 is connected to monitor the output from the strain gauge means 14 and to store the maximum output which is reached. When switch 56 is switched into its "peak" position, the display means 50 will provide a visual display of the peak force applied prior to failure. Switch 56 may also be switched into its "true" position when it is desired to monitor the actual force being applied by the testing device during a test operation.

Since a testing device of the type to which the present invention is directed may be used to test a large number of test samples, requiring the operator of the device to monitor the display 50 continually during each testing operation to determine if the test sample has withstood the required force would add substantially to operator fatigue. An adjustable pass level setting means for providing a pass level signal indicative of the force level which the material must withstand to pass successfully is therefore provided. A second switch means 60 is responsive to the output of the strain gauge means 14 and to the output of the sample means 54 for selectively providing either the peak signal on line 64 from the circuit 54 or, alternatively, the output of the strain gauge means 14 on line 66 to a comparator means 68.

The comparator means 68 acts as a "go/no go" circuit and energizes either diode 70 or diode 71 in dependence upon whether the signal provided to the comparator circuit 68 via switch 60 is greater than or less than the level set by resistor 69. Light emitting diodes 70 and 71 thus act as a pass indicator means for providing a visual indication of whether the test sample has withstood the force level set by resistor 69.

Figure 2:
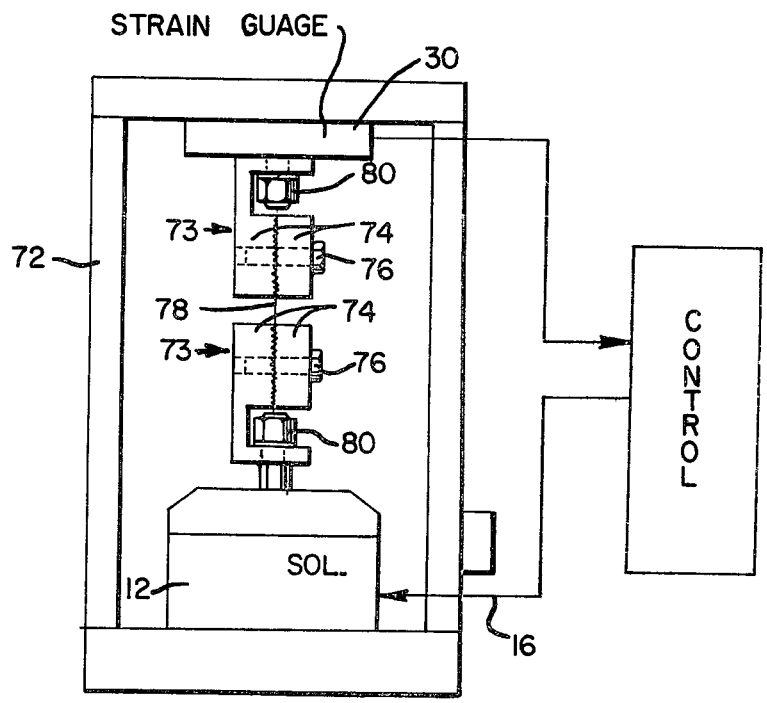
FIG. 2 is a front view of the test fixture, load cell, and solenoid of the testing device of the present invention.

The test fixture which engages the material test sample is illustrated in FIG. 2. A frame 72 has mounted thereon the strain gauge 30 and solenoid 12. The test fixture further includes a pair of sample gripping clamps 73. Each of the clamps 73 has a pair of plates 74 which are fastened together by means of bolts 76 to grip the material test sample 78. As illustrated, it may be desirable to provide a plurality of grooves in the mating surfaces of plates 74 in order to engage the test sample 78 more securely. Bolts 80 attach clamps 73 to the strain gauge 30 and the solenoid 12. When the solenoid 12 is energized, it will tend to pull the lower clamp 73 downward, thus placing the test sample 78 in tension.

A spring arrangement may be provided within the solenoid 12 to counterbalance the weight of the lower clamp 73 and the solenoid plunger such that when the solenoid 12 is not energized, no force will be applied to the test sample 78. Alternately, the test fixture may be mounted horizontally such that no force is applied to the test sample 78 by the weight of the lower clamp 73 and associated structure. The output from the strain gauge 30 is supplied to the control circuitry, as illustrated, which circuitry develops a control signal for application to line 16 for controlling solenoid 12. It will be appreciated that the specific construction of the test fixture may vary according to the nature of the test sample.

Figure 3A:
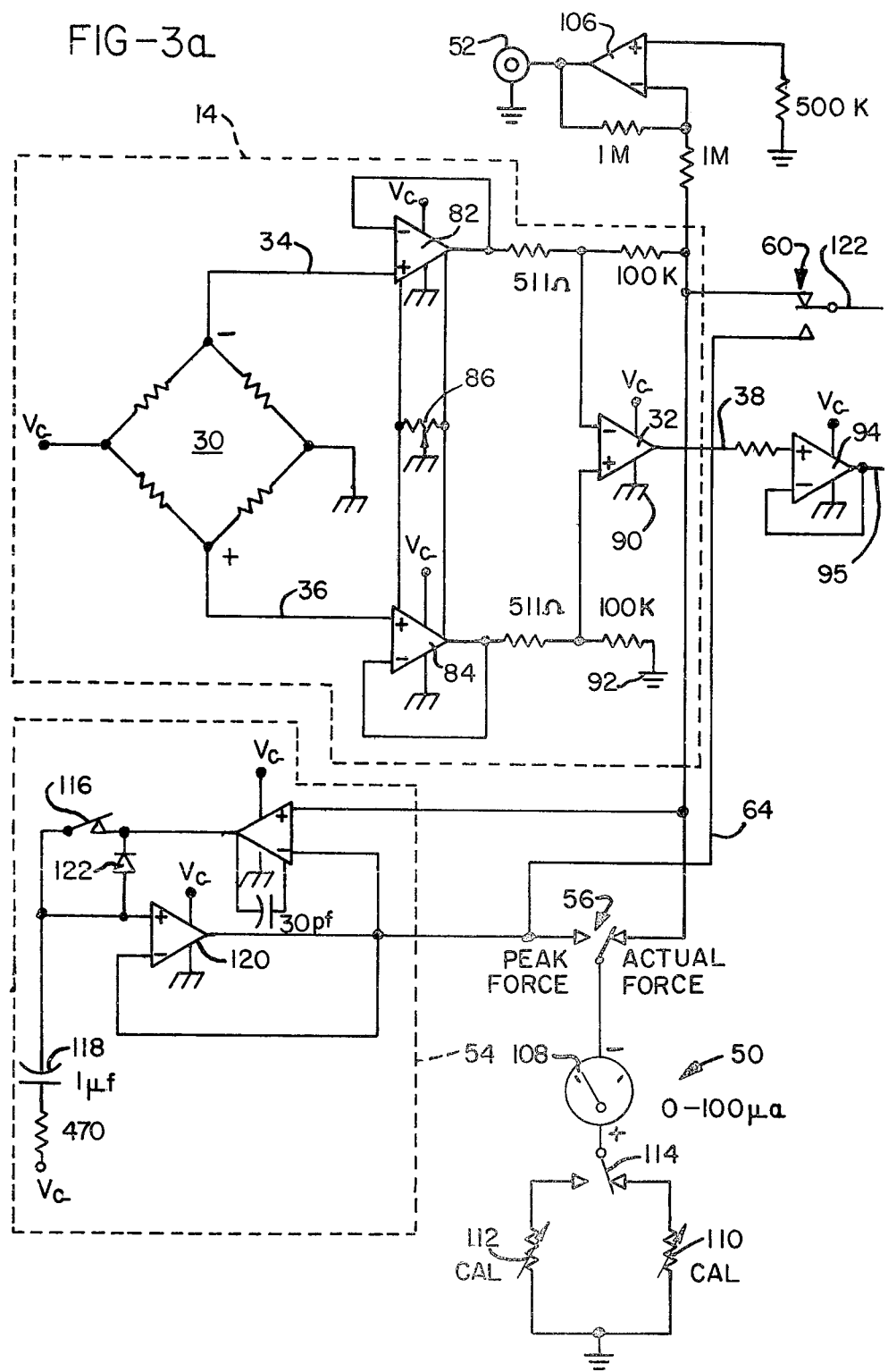

FIGS. 3A and 3B, when assembled with FIG. 3A to the left of FIG. 3B, illustrate the circuitry of the testing device of the present invention in greater detail. A strain gauge 30, of conventional design, provides outputs to line 34 and line 36 which are balanced when a zero force is applied to the test sample. As a force is applied to the strain gauge 30, however, the potential levels on lines 34 and 36 will diverge by a potential difference proportional to the force level applied to the test sample. The levels on line 34 and line 36 are applied through operational amplifiers 82 and 84 to differential amplifier 32. Resistor 86 provides null adjustment for the amplifiers. Amplifier 32 provides an electrical output on line 38 indicative of the force applied to the test sample.

When the strain gauge bridge 30 is balanced, a potential of 7.5 volts is applied to line 38. Ground 90 is held at 0 volts while ground 92 is maintained at 7.5 volts. As a force is applied to the test sample, the potential on line 38 will drop proportionally from 7.5 volts toward 0 volts. The output on line 38 is supplied through buffer amplifier 94 to node 40.

Also supplied to node 40 is the positive going ramp function from the ramp signal generator 24. The output of the ramp signal generator circuit 24 is held at 0 volts when switch 29 is in its off position, as illustrated. When switch 29 is switched to its on position, however, grounding the lower side of resistor 26, the inputs to integrator 96 will no longer be equal to $V_C$, nominally 15 volts, and therefore the integrator will begin integration at a rate determined by the voltage differential between its inputs. Line 22 will therefore receive a ramp signal which will increase at a rate set by resistor 26. Buffer amplifier 98 and diode 100 form a clamping circuit which prevents the output on line 22 from exceeding the potential level set by resistor 28, thus providing a means for limiting the increasing electrical output on line 22 to an adjustable maximum level. The maximum force which may be applied to the test sample is thereby set. The potential applied at node 40 thus is an indication of the difference between the force desired to be applied to the test sample and the force which is actually applied to the test sample. This error signal is applied through the summing amplifier 42 to node 48.

Also applied to node 48 is the output from the saw tooth oscillator 44. Oscillator 44 provides a constant frequency, saw tooth shaped, oscillating output of approximately 1 KHz. The frequency of the oscillating output is not critical but it should be chosen to exceed 700 KHz. At lower frequencies the solenoid 12 might respond to each cycle of the pulse width modulated signal on line 16 to cause a "chatter" effect. The output of oscillator 44 is summed with the DC output from the summing amplifier 42 at node 48 and compared with a 7.5 volt constant level by amplifier 102. When the input to amplifier 102 from node 48 drops below the 7.5 volt threshold, the output of the amplifier will switch transistor 104 ON, thus energizing solenoid 12. Thus, it is seen that the DC potential level supplied by the summing amplifier 42 to node 48 determines the period of time during each cycle of the output of oscillator 44 that the saw tooth output will exceed the reference level. As the potential level at node 48 supplied by amplifier 42 decreases, the transistor 104 will be switched on for correspondingly greater periods of time during each cycle of the oscillator 44. A pulse width modulated signal will thereby be provided from the solenoid power supply potential $V_p$ to the solenoid 12 to control the force applied by the solenoid to the test sample.

The output from the differential amplifier 32 is also applied to a recorder output 52 via a buffer amplifier 106. This output may be used to control the operation of a strip chart recorder or other recording device.

The output of differential amplifier 32 is also supplied to the display means 50, including meter 108, for displaying visually the force level applied to the test sample. Meter 108 may comprise a 0–100 microamp ammeter with resistors 110 and 112 being selectively connected to the meter 108 by switch 114 to provide a choice of maximum scale reading.

The sample means 54 is responsive to the output of differential amplifier 32 for providing a peak signal indicative of the maximum output from the strain gauge means 14. Operation of the circuit 54 is initiated by opening switch 116. If desired, this switch may be mechanically linked to switch 29 to initiate operation of circuit 54 at the beginning of each testing operation. Capacitor 118 will therefore be charged as the output of the differential amplifier 32 drops below 7.5 volts. Buffer amplifier 120 provides an output indicative of the charge level of capacitor 118 to the switch 56. Should the force applied to the test sample be reduced, the output on line 38 will increase. The diode 122 will, however, be reverse biased in such an event, maintaining the charge on capacitor 118.

An adjustable pass level setting means including resistor 69 provides a pass level signal indicative of a force level which the test sample must withstand to pass successfully. Switch 60 comprises a second switch means, responsive to the strain gauge means 14 and to the sample means 54, for selectively providing the peak signal or the output of the strain gauge means to the line 122.

Amplifier 124 acts as a comparator means, responsive to the pass level signal from resistor 69 and to the output of the second switch means, for providing a pass indication signal to line 126 when the output from the switch 60 exceeds the pass level signal. Light emitting diodes 70 and 71 are responsive to the pass indication signal from the amplifier 124 for providing a visual indication of whether the test sample has withstood the required force level and thereby passed the test. By setting switch 60 so as to connect circuit 54 to the comparator means 68, it may be determined whether the force applied to a test sample exceeded the pass level set by resistor 69, even if the test sample subsequently failed when a greater force was applied thereto.

Since the solenoid 12 will be required to operate over a small axial range in the testing of most materials, an inexpensive variable air gap axial unit may be used. For example, a particularly efficient and effective actuator is the solenoid described in the U.S. Pat. No. of Leland, 3,264,530, issued Aug. 21, 1966, with the rotary balls 44 removed to convert it from rotary to axial operation. In instances where longer strokes are desired, the solenoid described in the U.S. Pat. No. 3,900,822, issued Aug. 19, 1975, to Hardwick et al may be used.

It should be appreciated that the present invention may be utilized for compressive testing as well as tensile testing of test samples. In order to apply a compressive force to a test sample, it will be appreciated that the construction of the test fixture, including the clamps holding the test sample, would require modification. Additionally, the solenoid 12 shown in FIG. 2 would be required to apply an upward force to the sample.

While the form of apparatus herein described constitutes a preferred embodiment of the invention, it is to be understood that the invention is not limited to this precise form of apparatus, and that changes may be made therein without departing from the scope of the invention.

What is claimed is:
1. A testing device for applying a force to a material test sample, comprising:
   a test fixture for engaging the test sample,
   a solenoid, operatively coupled to said test fixture, for applying a force to said test sample in response to a solenoid control signal, strain gauge means, mounted on said test fixture, for providing an electrical output indicative of the force applied to said test sample, force setting circuit means for providing an electrical output indicative of the predetermined force which is to be applied to said test sample, and solenoid control circuit means, responsive to the output from said strain gauge means and to the output from said force setting means, for providing a pulse width modulated solenoid control signal to said solenoid, whereby a predetermined force may be applied to said test sample.

2. The testing device of claim 1 in which said force setting circuit means comprises means for providing an increasing electrical output and means for setting the rate of increase of said increasing electrical output.

3. The testing device of claim 2 in which said force setting means further comprises means for limiting said increasing electrical output to an adjustable maximum level, whereby the maximum force which may be applied to said test sample is set.

4. The testing device of claim 1, further comprising display means, responsive to said strain gauge means, for providing a visual display of the force applied to said test sample.

5. The testing device of claim 4, further comprising:

sample means, responsive to said strain gauge means, for monitoring the output from said strain gauge means and for providing a peak signal indicative of the maximum output from said strain gauge means, and switch means for selectively connecting said sample means to said display means, whereby the peak force applied to said test sample may be determined and displayed.

6. The testing device of claim 5, further comprising:

adjustable pass level setting means for providing a pass level signal indicative of a force level which said test sample must withstand to pass successfully, second switch means, responsive to said strain gauge means and to said sample means, for selectively providing said peak signal or the output of said strain gauge means to the output of said second switch means, comparator means, responsive to said pass level signal and to said output of said second switch means, for providing a pass indication signal when said output of said second switch means exceeds said pass level signal, and pass indicator means, responsive to said pass indication signal, for providing a visual indication of whether said test sample has passed.

7. A testing device for applying a force to a material test sample, comprising a support fixture, a first sample engaging clamp fixedly mounted on said support, a second sample engaging clamp, an axial solenoid mounted on said fixture having a coil and a moving armature, means connecting said second clamp directly to the armature of said solenoid for applying a force to said sample in response to a solenoid control signal, strain gauge means, mounted on said fixture, for providing an electrical output indicative of the force applied to said sample, force setting circuit means for providing an electrical output indicative of the predetermined force which is to be applied to said sample, and solenoid control circuit means, responsive to the output from said strain gauge means and to the output from said force setting means, for providing a pulse width modulated solenoid control signal to said solenoid coil, whereby a predetermined force may be directly applied to said sample.

8. A testing device for applying a force to a material test sample, comprising:

a test fixture for engaging the test sample, a solenoid, operatively coupled to said test fixture, for applying a force to said test sample in response to a solenoid control signal, strain gauge means, mounted on said test fixture, for providing an electrical output indicative of the force applied to said test sample, force setting circuit means for providing an electrical output indicative of the predetermined force which is to be applied to said test sample, solenoid control circuit means, responsive to the output from said strain gauge means and to the output from said force setting means, for providing a control signal to said solenoid, whereby a predetermined force may be applied to said test sample, display means, responsive to said strain gauge means, for providing a visual display of the force applied to said test sample, sample means, responsive to said strain gauge means, for monitoring the output from said strain gauge means and for providing a peak signal indicative of the maximum output from said strain gauge means, switch means for selectively connecting said sample means to said display means, whereby the peak force applied to said test sample may be determined and displayed, adjustable pass level setting means for providing a pass level signal indicative of a force level which said test sample must withstand to pass successfully, second switch means, responsive to said strain gauge means and to said sample means, for selectively providing said peak signal or the output of said strain gauge means to the output of said second switch means, comparator means, responsive to said pass level signal and to said output of said second switch means, for providing a pass indication signal when said output of said second switch means exceeds said pass level signal, and pass indicator means, responsive to said pass indication signal, for providing a visual indication of whether said test sample has passed.

* * * * *